United States Patent [19]
Lee et al.

[11] Patent Number: 5,939,332
[45] Date of Patent: Aug. 17, 1999

[54] PHENCYCLIDINE ANALOGS FOR IMMUNOASSAY

[75] Inventors: James C. Lee; Luis Fernando Del Corral, both of Memphis; Richard A. Clark, Collierville; Pedro A. Bonilla, Memphis, all of Tenn.

[73] Assignee: Roche Diagnostics Corp., Indianapolis, Ind.

[21] Appl. No.: 09/032,158

[22] Filed: Feb. 27, 1998

[51] Int. Cl.$^6$ ................ G01N 33/544; C07D 409/10; C07D 207/04
[52] U.S. Cl. ............... 436/530; 436/534; 436/815; 546/202; 546/213; 548/567
[58] Field of Search ................. 436/500, 534, 436/815; 546/202, 213; 548/567

[56] References Cited

U.S. PATENT DOCUMENTS

| | | | |
|---|---|---|---|
| 4,196,185 | 4/1980 | Focella et al. | 546/194 |
| 4,281,065 | 7/1981 | Lin et al. | 435/188 |
| 4,446,065 | 5/1984 | Lin et al. | 435/188 |
| 5,124,457 | 6/1992 | Ungemach et al. | 546/196 |
| 5,144,030 | 9/1992 | Wang et al. | 546/89 |
| 5,155,212 | 10/1992 | Dubler et al. | 530/408 |
| 5,221,629 | 6/1993 | Ungemach et al. | 436/536 |
| 5,237,057 | 8/1993 | Buechler et al. | 536/119 |
| 5,331,109 | 7/1994 | Buechler | 530/404 |
| 5,407,834 | 4/1995 | Dubler et al. | 436/537 |

OTHER PUBLICATIONS

Budd et al., J. Toxicol.: Clin. Toxicol, 19(8):843–850 (1982).
Heveran, Journal of Forensic Sciences, 25(1):79–87 (1980).
Kalir et al., Theriogenology 6(2–3):193–208 (1976).
ŠindelářR Collect. Czech. Chem. Commun. 60:894–902 (1995).
Wall et al., Research Communications in Substance Abuse, 2(2):161–172 (1981).

*Primary Examiner*—Mary E. Ceperley
*Attorney, Agent, or Firm*—W. Scott McNees; Marilyn L. Amick

[57] ABSTRACT

Novel analogs of phencyclidine (PCP) are disclosed. The analogs are capable of reacting with anti-PCT antibodies and are useful in immunoassays.

The following analogs are described:

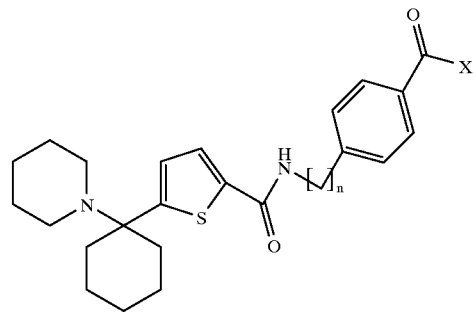

and

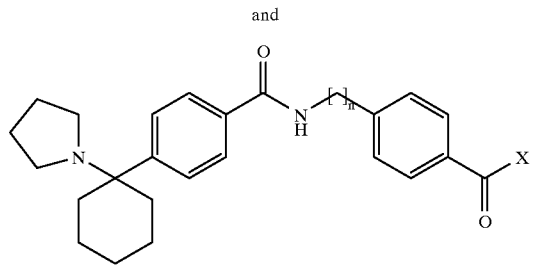

wherein wherein X is —OH or a reporter molecule selected from the group consisting of aminofluorescein and aminomethylfluorescein and n is an integer between 1 and 10, inclusive.

9 Claims, 3 Drawing Sheets

PHENCYCLIDINE ANALOGS FOR IMMUNOASSAY

BACKGROUND AND SUMMARY OF THE INVENTION

Phencyclidine 1-(1-phenylcyclohexyl piperidine), known as PCP was originally used as an anesthetic agent. PCP has become prevalent in the elicit drug market. It is often sold as "angel dust", "dust" or "super grass". The compound is a potent drug with lethal potential. and has become a major drug abuse problem. In 70 cases where PCP was deemed a factor in death, 90% of the cases had blood levels ranging from 10 to 300 ng/mL [R. Budd and Y. Liu (1982). phencyclidine Concentration in Postmortem Body Fluids and Tissues. J. Toxicol. Clin Toxicol. 19(8):843–850]. PCP is extensively metabolized and about 10% is excreted unchanged in urine [M. Wall, D. Brine, A. Jeffcoat et al. (1981). Phencyclidine Metabolism and Disposition in Man following 100 mcg Intravenous Dose. Res Comm. in Substances Abuse. 2:161–172]. The NIDA cut-off value requires at least 25 ng/mL before a measurement may be reported as positive. Thus it is desirable to have a simple and rapid technique for detecting the presence of PCP in body fluid such as blood plasma and urine. It is additionally desirable to prevent cross-reactivity to other drugs which may be present and have clinically similar symptoms. For this purpose, it is desirable to develop immunogenic conjugates of the phencyclidine hapten to elicit antibodies which provide the required degree of specificity while having high binding affinities and titer.

A radioimmunoassay for PCP is described by Kalir et al. (1976), Theriogenology 6, No. 2–3, 193. This assay employed $^3$H-labeled phencyclidine derivative as $^3$H-4—aminophenyl phencyclidine. The use of radioisotope is undesirable because of the waste generated from it. PCP derivative having a non-oxo carbonyl functionality linked directly or through a linking group out of the phenyl ring of PCP is described by C-I Lin, and P. Singh (1981), U.S. Pat. No. 4,281,065. This compound is used as the derivative for an enzyme immunoassay. Another PCP derivative having an oxime functionality linked out of the cyclohexane ring of the PCP molecule is described by C-I Lin, and P. Singh (1984), U.S. Pat. No. 4,446,065. This compound is employed as the derivative for an enzyme immunoassay. Still another compound having a carboxy functionality linked directly or through a linking group out of the phenyl ring of PCP is described by A. Focella (U.S. Pat. No. 4,196,185; 1980) and J. E. Heveran (J. Forensic Sciences, 25:79–87,1980). This compound and its derivatives are used in an immunoassay. Further compounds having an N-functionality fused to a piperidine ring of PCP are described in U.S. Pat. No. 5,221,629 (1993), U.S. Pat. No. 5,124,457 (1992), U.S. Pat. No. 5,407,834 (1995), and U.S. Pat. No. 5,155,212 (1992). All of these derivatives including tracers and immunogens described above are made from a ring-substituted phencyclidines all of which posses the core structure derived from phencyclidine itself, the structure of which is shown below phencyclidine

DETAILED DESCRIPTION OF THE INVENTION

The present invention is directed toward novel analogs having structures similar to phencyclidine (PCP). These analogs are 4-phenyl-4-pyrrolidinocyclohexane, thienylcyclohexylpiperidine (Tenocyclidine) and thienylcyclohexypyrrolidine having substituents on the aryl and thiophene rings as represented in formula I, II and III as shown below. These compounds do not possess the exact core structure of PCP as shown above but instead possess structures which are different in at least one of the cyclic components of the core. These analogs are capable of binding with antibodies against PCP. The substituents on these analogs can be linked to a variety of reporter molecules and protein carriers to provide useful reagents for immunoassay. When combined with the PCP antibodies, the compounds and the corresponding protein conjugates described in the present invention provide for sensitive and rapid assay for the detection of PCP in human urine.

A functional group is a chemical group which can be converted by chemical means to another functional group for altering or enlarging the compound. For example, a compound which bears a carboxy functional group can be reacted with an amine bearing linker such as a aminoacid with the aid of a carbodiimide and the like, but not limited to other similar compounds, to form a compound of new entity bearing a peptide bond or an amide bond. Conversely, a compound bearing an amine can be coupled to a linker bearing a carboxy with the aid of carbodiimide to form compound-linker conjugate bearing a peptide bond. This process of linking carboxy to amine is well known in the art and it represents the simplest method for making a peptide conjugate or compound-protein conjugate (herein called drug-conjugate).

Linkers are well known in the art and are commonly used to provide a spacer between a compound and a carrier molecule or a reporter molecule. Use of a linker may or may not be advantageous depending on the specific compound or hapten and the carrier pairs, and selection of an appropriate linking group is within the skill of the art. See U.S. Pat. No. 5,144,030 (column 16, line 1) and U.S. Pat. No. 5,237,057 (column 2). Typical linker will vary from 1–20 carbon atoms of straight or branched chain and 0–5 heteroatoms of N, O, and S. It is well known to those skilled in the art that combination of atoms or functional groups which are compatible can form the linking to allow covalent bonding of the compound and the carrier or reporter molecule. In many cases the use of linker requires more steps than direct coupling of a carboxy bearing compound to an amine. For example, compounds bearing a thiol functionality may react with a carrier molecule bearing thiol-reactive groups, such as maleimide groups, as exemplified by U.S. Pat. No. 5,237,057. This process of linking drugs to protein carriers involves more steps than direct approach described in this invention.

A reporter molecule is a carrier molecule which bears an appropriate functional group ready for covalent bonding with aid of carbodiimide and the like. Examples of carrier molecules are thyroglobulin (BTG), bovine serum albumin (BSA), enzymes, and aminoacids including polyaminoacids. Other reporter molecules include fluorescein which bear an amine or carboxy function such as aminofluorescein and carboxyfluorescein (Molecular Probe, Eugene, Oreg.).

In a preferred embodiment of the present invention a novel compound represented as formula I is useful for the preparation of the protein conjugate.

I wherein:
X is a bond, —O—, —NH— or a linker consisting of an aminoacid but not limited to poly(aminoacid), aminomethylbenzoic acid where the amine function is attached to the oxo carbonyl,
Y is —H, or a reporter molecule such as aminofluorescein and aminomethylfluorescein where the amine function is linked to the oxo carbonyl of X, protein carrier or enzyme where it is attached in the same manner to the X group.

Alternatively, another preferred embodiment of the present invention is a novel compound with its substituent having formula II that is useful for the preparation of the protein conjugate.

II wherein:
X is a linker, —O—, —NH— consisting of an aminoacid but not limited to poly(aminoacid), aminomethylbenzoic acid where the amine function is attached to the oxo carbonyl,
Y is a —H or reporter molecule such as aminofluorescein and aminomethylfluorescein where the amine function is linked to the oxo carbonyl end of X, BSA, protein carrier or enzyme where they are attached in the same manner to the X group.

Still another variation of compound having similar structure to formulas I and II as described above are useful. This is represented as formula III

III wherein:
X is a linker, —O—, —NH—consisting of an aminoacid but not limited to poly(aminoacid), aminomethylbenzoic acid where the amine function is attached to the oxo carbonyl,
Y is —H, a reporter molecule such as aminofluorescein and aminomethylfluorescein where the amine function is linked to the oxo carbonyl end of X, BSA, protein carrier or enzyme where they are attached in the same manner to the X group.

In order to prepare novel analogs having the general structure of formula I, cyclohexanone was used as the starting material. This compound was condensed with pyrrolidine in the presence of KCN and sulfuric acid to provide compound 1 which was further carried forward to compound 3 according to methods described in Scheme I below.

Scheme I

The carboxy group of compound 3 can be linked to a variety of reporter molecule and aminoacids to provide useful reagents for immunoassay use. In a preferred embodiment, extension of compound 3 at the carboxy functionality with aminomethyl benzoic acid aided by EDC and NHS provided compound 5. This compound provided the most preferred reagent when coupled to BSA as described elsewhere in this invention.

Another variation of compound of formula I having a substituent at the para-position of the aryl ring can be prepared according to Scheme II as shown below. For example, carboxy derivative 8 was activated to provide the N-hydroxysuccinimide derivative 9. This activated compound can be coupled to a variety of reporter molecules to provide a useful reagent for an immunoassay to detect PCP in urine and other body fluid.

Scheme II

Substitution of Tenocyclidine at the C-5 position of thienyl ring that leads to the carboxy Tenocyclidine 10, can be prepared according to method described by K. Sindler, Collect. Czech. Chem. Commun. 60:894–902(1995) Although this compound can be coupled to BSA to make useful Tenocyclidine conjugate, it is preferable that a linker such as aminomethylbenzoic acid as described in Scheme III be used and coupled at the carboxy end to provide compound 12. This is highly desirable as the resulting compound is highly chromogenic to allow ease of quantitation of the degree of drug substitution after coupling to proteins. Certainly other chromogenic molecules would be useful as well for substituting aminomethylbenzoic acid. This will aid in the determination of the drug incorporation on proteins. Scheme III illustrates the preparation of compound 12 and the corresponding N-hydroxysuccinimide ester 13 which can be linked to various reporter molecules.

Another novel derivative of Tenocyclidine substituted at the C-5 of the thiphene ring was obtained by direct succinylation of Tenocyclidine using aluminum chloride to provide compound 14 according to the preparation described in Scheme IV. This carboxy derivative can be linked to a variety of reporter molecules useful for immunoassay.

-continued

14

In order to prepare compounds of formula III which bears pyrrolidine in the molecule, compound 1 can be utilized as the starting molecule. First, thiophene can be treated with n-butyl lithium to provide 2-lithiothiophene. Alternatively, 2-bromothiophene can be converted to the corresponding Grignard reagent. Among the two reagents, thiophene, 2-magnesium Grignard is the preferred reagent and can be reacted with compound 1 described previously to afford the Tenocyclidine analog bearing the pyrrolidine ring. Functionalization at the C-5 position of the thiophene ring can be carried out analogously according to methods described in Scheme III and IV above.

Other components required for the PCP immunoassay described in this invention are antibodies that recognize or bind to PCP itself. Immunogens containing PCP may elicit polyclonal antibodies to bind PCP. The PCP immunogen and the antisera were prepared according to the method described by Focella in U.S. Pat. No. 4,196,185.

The novel compounds described in this present invention can be used in a variety of immunoassays for the detection of PCP and its metabolite. Such immunoassays may be in the form of radioimmunoassay, enzyme immunoassays or microparticle-based immunoassay in which agglutination of microparticles represents the signal detection and others. Immunoassays for PCP are commonly based on competitive binding between drug derivatices coupled to protein carrier, and free drug from a clinical sample for a limiting amount of antibodies. Free drug will inhibit the binding of the drug derivatives to the antibody. The extent to which the free drug inhibits the binding of the drug derivatives to the antibody is a direct measurement of the amount of drug present in the clinical sample.

Figure 1:
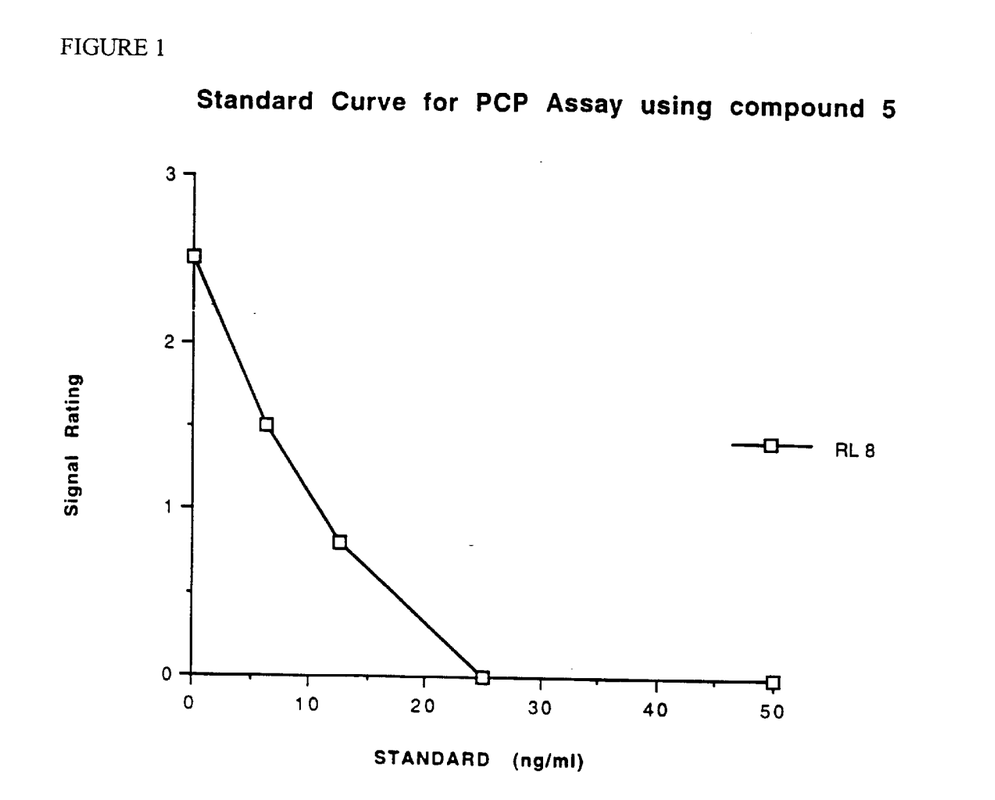
FIG. 1 illustrates competition between compound 5 and PCP.
Figure 2:
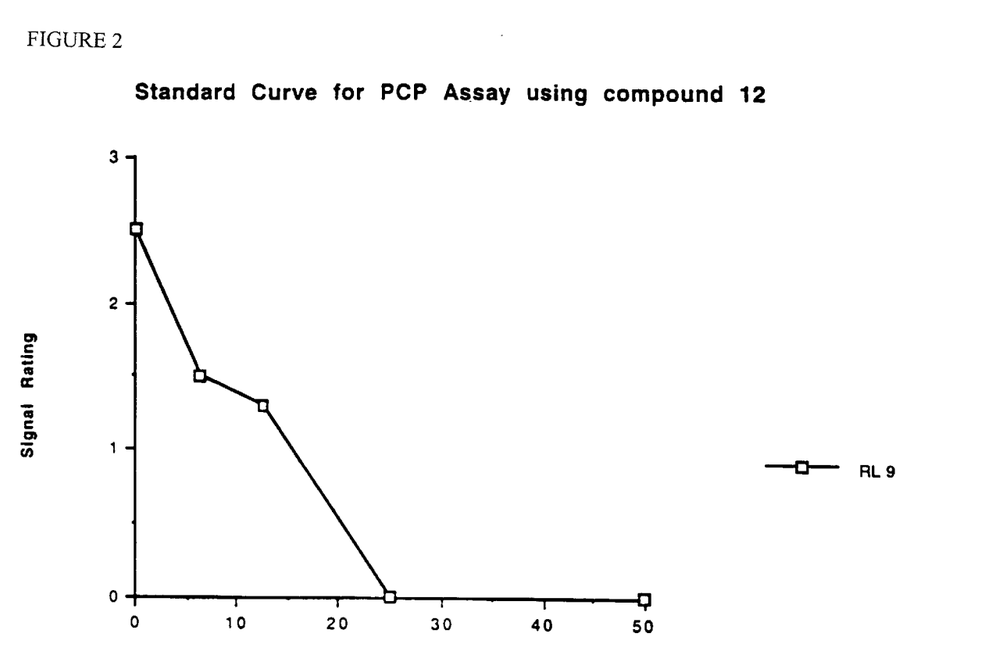
FIG. 2 illustrates competition between compound 12 and PCP.

In a preferred embodiment of the present invention, drug derivatices are couples to BSA according to the coupling of carboxy to amine as described previously. Antibodies against PCP are bound onto microparticles by passive adsorption on the surface of microparticle. Both materials were then placed onto membrane strips as described in Example 17 and the calibration curve or assay run as described also in Example 17. The standard curve shown in FIG. 1 illustrates how novel compound 5 derived from the present invention, when coupled to BSA competes with free drug (PCP) for anti-PCP antibodies such on dyed microparticles that the presence of PCP results in a decrease or inhibition of the antibody-drug interaction and that this compound is useful as a reagent for the determination of PCP. FIG. 2 illustrates how drug-BSA conjugate derived from compound 12 competes similarly with free drug (PCP) for the anti-PCP antibodies on dyed microparticles such that the presence of PCP results in an inhibition of the antibody-drug derivative interaction and that this compound is useful as a reagent for the determination of PCP.

Another preferred embodiments of immunoassays in which the compounds of the invention are useful is described in copending U.S. pat. application Ser. No. 877, 189, the entire contents of which is hereby incorporated by reference. Such an assay is marketed by Roche Diagnostic Systems under the trademark OnTrak TestTstick™ for PCP. The assay is based on the principles of microparticle capture inhibition. The test relies on the competition between drug, which may be present in the urine being tested, and drug conjugate immobilized on membrane for binding to antibody-coated onto colored microparticles.

When the device is immersed in the urine sample, some of the sample is absorbed into the sample pad. The absorbed sample travels through a reagent strip contained in the device by capillary action. In the reagent strip, the sample rehydrates and mobilizes antibody-coated blue microparticles. The microparticle-urine suspension continues to migrate through the reagent strip and comes in contact with the immobilized drug conjugate. In the absence of drug in the urine, the antibody-coated microparticles bind to the drug conjugated and a blue band is formed at the result window ("negative" sign).

When drug is present in the specimen, it binds to the antibody-coated microparticles. If sufficient drug is present, the microparticles are inhibited from binding the drug conjugate and no blue band is formed at the result window. A positive sample causes the membrane to remain white ("positive" sign).

An additional antibody/antigen reaction occurs at a "TEST VALID" area. The "TEST VALID" blue band forms when anti-bodies, which are imbedded in the reagent membrane, bind to the antigen on the blue microparticles. The presence of the "TEST VALID" band indicates that the test has completed, the reagents are viable, and, the results are ready to interpret.

EXAMPLE 1

Preparation of 1-Pyrrolidin-1-yl-cyclohexanecarbonitrile, (Compound 1)

To a magnetically stirred mixture of 5.0 g pyrrolidine (70.3 mmol) in 12 mL of ice-cold deionized water was added 5 mL of concentrated $H_2SO_4$. The pH of the reaction mixture was adjusted to 3.5 with concentrated $NH_4OH$. The reaction was cooled to 20° C. and 6.9 g (70.2 mmol) of cyclohexanone was added followed by a solution of 4.57 g (70.2 mmol) of potassium cyanide in 10 mL of water. The mixture was stirred at room temperature for 18 h. The reaction mixture was filtered and the filtrate was concentrated. This was dissolved in 200 mL of dichloromethane and 80 mL of brine was added. The organic layer was separated and the aqueous part was extracted with 2×100 mL of dichloromethane. The combined organic layer was dried with an anhydrons $Na_2SO_4$ and concentrated to give 7.2 g (40.4 mmol, 58%) of compound 1 as colorless oil.

EXAMPLE 2

Preparation of 1-[1-(3-Trifluoromethyl-phenyl)-cyclohexyl]-pyrrolidine, (Compound 2)

A 250 mL three-necked round-bottom flask was charged with 2.12 g of magnesium turning and 100 mL of freshly distilled tetrahydrofuran under argon atmosphere. To the reaction mixture was added 4.42 g (13 mmol) of 3-bromotrifluoromethanebenzene followed by 250 μL of 1,2 dibromoethane and a catalytic amount of iodine crystal. The mixture was allowed to reflux for 4 h under argon atmosphere and cool to room temperature. A solution of 2 g (11.2 mmol) of compound 1 in 15 mL of freshly distilled tetrahydrofuran was added to the reaction mixture dropwise and this was allowed to stir for 18 h at room temperature. The reaction mixture was filtered and 60 mL of a saturated solution of ammonium chloride was added to the filtrate. The aqueous layer was extracted with 3×100 mL of ethyl acetate. The combined ethyl acetate layer was washed with 100 mL of brine, dried with anhydrous $Na_2SO_4$ and concentrated. The residue was purified by column chromatography using 1:1 ethyl acetate: hexane to provide 1.85 g (6.29 mmol, 57%) of compound 2.

EXAMPLE 3

Preparation of 3-(1-Pyrrolidin-1-cyclohexyl)-benzoic acid, (Compound 3 )

A mixture of 1 g (3.40 mmol) of compound 2 and 2.5 mL of concentrated $H_2SO_4$ was heated in an oil bath at 110° C. for 2 h. The reaction mixture was cooled to room temperature and 5 mL of ice-water was added. The pH of the solution was adjusted to 7 and concentrated to dryness. The residue was triturated with 300 mL of 20% methanol in dichloromethane and the inorganic residue was filtered off. The filtrate was concentrated to give 902 mg (3.30 mmol, 97%) of compound 3 as off-white solid.

EXAMPLE 4

Preparation of 3-(1-Pyrrolidin-1-yl-cyclohexyl)-benzoic acid 2,5-dioxo-pyrrolidin-1-yl ester, (Compound 4)

To a solution of 750 mg(2.74 mmol) of compound 3 was added 790 mg (4.12 mmol) of 1-ethyl-3(3dimethylamino-propyl)carbodiimide and 473 mg (4.10 mmol) of N-hydroxysuccinimide. The mixture was allowed to stir at room temperature 18 h and 30 ml of dichloromethane was added. The organic layer was washed with 2×50 mL of water, 2×50 mL of saturated $NaHCO_3$ and 50 mL of water. The organic layer was dried $Na_2SO_4$ and concentrated to give 830 mg (2.24 mmol, 82%) of compound 4 as white solid.

EXAMPLE 5

Preparation of 4-{([3-(1-Pyrrolidin-1-yl-cyclohexyl) benzoylamino]-methyl}-benzoic acid, (Compound 5 )

To 688 mg (4.55 mmol) of aminomethylbenzoic acid was added 4.4 mL of 1N NaOH, 50 mL THF and 16 mL of water. The N-hydroxysuccinimidyl ester compound 4 (1.62 g, 4.3 mmol) was dissolved in 32 mL of freshly distilled THF and added dropwise to the above solution. After the addition the reaction mixture appeared cloudy. An additional 12 mL of water was added and the pH was maintained at 9–10 for 2 h. The reaction mixture was concentrated to remove as much THF as possible. The residual aqueous part was adjusted to 6.5 and extracted with chloroform (10×50 mL). The combined organic layer was dried (anh. $Na2SO_4$) and concentrated to give 1.4 g(3.4 mmol, 79%) of compound 5 as white solid.

EXAMPLE 6

Preparation of 4-{[3-(1-Pyrrolidin-1-yl-cyclohexyl) benzoylamino]-methyl}-benzoic acid 2,5-dioxo-pyrrolidin-1-yl ester, (Compound 6)

To a mixture of 1.2 g ( 2.95 mmol) of compound 5 in 240 mL of dichloromethane was added 550 mg of N-hydroxysuccinimide and 917 mg of EDC hydrochloride. The reaction mixture was allowed to stir at room temperature for 18 h and washed with brine (2×125 mL), 2×125 mL of saturated $Na_2CO_3$ and water (125 mL). The organic layer was dried ($Na_2SO_4$) and concentrated. The residue was purified by column chromatography to give 800 mg (1.58 mmol, 56%) of compound 6 as white solid. Likewise, compound 9 was converted to compound 15 in the same manner.

EXAMPLE 7

Preparation of 1-[1-(4-Trifluoromethyl-phenyl)-cyclohexyl] pyrrolidine, (Compound 7)

A 250 mL three-necked round-bottom flask was charged with 2.12 g of magnesium turning and 100 mL of freshly distilled tetrahydrofuran under argon atmosphere. To the reaction mixture was added 4.42 g (13 mmol) of 4-bromotrifluoromethanebenzene followed by 250 μL of 1,2dibromoethane and a catalytic amount of iodine crystal. The mixture was allowed to reflux for 4 h under argon atmosphere and cool to room temperature. A solution of 1 g (5.6 mmol) of compound 1 in 15 mL of freshly distilled tetrahydrofuran was added to the reaction mixture dropwise and this was allowed to stir for 18 h at room temperature. The reaction mixture was filtered and 60 mL of a saturated solution of ammonium chloride was added to the filtrate. The aqueous layer was extracted with 3×100 mL of ethyl acetate. The combined ethyl acetate layer was washed with 100 mL of brine, dried (anh. $Na_2SO_4$) and concentrated. The residue was purified by column chromatography using 1:1 ethyl acetate: hexane to provide 910 mg (3.06 mmol, 55%) of compound 7 as colorless gum.

EXAMPLE 8

Preparation of 4-(1-Pyrrolidin-1-cyclohexyl)-benzoic acid, (Compound 8 )

A mixture of 4.3 g (14.4 mmol) of compound 7 and 10 mL of concentrated $H_2SO_4$ was heated in an oil bath at 110° C. for 1.5 h. The reaction mixture was cooled to room temperature and was added to 15 mL of ice-water. The pH of the solution was adjusted to 7.5 using 6N NaOH. During the neutralization procedure some black material started to form which was filtered off and the neutralization procedure continued to adjust the pH to 7.5. A white precipitate formed. This was left at room temperature 18 h and filtered to give 3.9 g(14.2 mmol, 99%) of compound 8.

EXAMPLE 9

Preparation of 4-(1-Pyrrolidin-1-yl-cyclohexyl)-benzoic acid 2,5-dioxopyrrolidin-1-yl ester, Compound 9)

To a solution of 1 g(3.65 mmol) of compound 8 in 100 mL of dichloromethane was added 1.8 g (9.38 mmol) of 1-ethyl-3(3-dimethylamino-propyl)carbodiimide and 1.0 g (8.68 mmol) of N-hydroxysuccinimide. The mixture was allowed to stir at room temperature 18 h. The organic layer was washed with 2×100 mL of water, 2×100 mL of saturated $NaHCO_3$ and 2×100 mL of brine. The organic layer was dried (anh. $Na_2SO_4$) and concentrated. The crude product was purified by silica gel chromatography using ethyl acetate as eluent to give 1.18 g (3.18 mmol, 87%) of compound 9 as pale yellow amorphous solid.

EXAMPLE 10

Synthesis of the TCP Analog (Compound 10)

1.76 mL (4.41 mmol) of n-butyl lithium, 2M in hexane, was added to a solution of 1 g (4.01 mmol) of Tenocyclidine (TCP) in 50 mL of anhydrous $Et_2O$ (distilled from sodium/benzophenone) cooled to 0° C. in an ice bath under argon. The cooling bath was removed, and the reaction was stirred for 45 min at ambient temperature. The reaction was then cooled back down to 0° C., and $CO_2$(g) was bubbled into the reaction for ~5 min. The reaction was poured into 150 mL of $H_2O$ forming a thick emulsion which contained an insoluble precipitate and slowly separated on standing. The aqueous phase was washed with 3×100 mL of $ET_2O$, and then filtered to collect the precipitate which was dried under vacuum to give 459 mg (39% yield) of compound 10 as a white solid. A second crop of product was obtained by adjusting the pH of the filtered aqueous layer to 6 to 7 with 1N HCl, and the solution was allowed to stand at 4° C. overnight. The precipitate which formed was filtered to give an additional 197 mg (17% yield) of compound 10.

EXAMPLE 11
Synthesis of the TCP Analog, (Compound 11)

A suspension of 300 mg (1.02 mmol) of compound 10, 586 mg (5.09 mmol) of N-hydroxysuccinimde and 488 mg (2.55 mmol) of 1-(3-dimethylaminopropyl)-3ethylcarbodiimide hydrochloride in 5 mL of anhydrous DMF and 20 mL of anhydrous $CH_2Cl_2$ (distilled from $CaH_2$) was stirred overnight at ambient temperature under argon. The reaction mixture was filtered through Whatman #1 filter paper to remove unreacted starting material, and then diluted to 100 mL with $CH_2Cl_2$. The reaction was washed twice with 100 mL of sat. $NaHCO_3$ and once with 100 mL of $H_2O$, dried over $Na_2SO_4$, and the solvent was removed under reduced pressure. The resulting material was purified by chromatography on flash grade silica eluted with 1:1:1 THF (distilled from sodium/benzophenone)/EtOAc/hexane to give 258 mg (65% yield) of compound 11 as a white solid.

EXAMPLE 12
Synthesis of the TCP Analog, (Compound 12)

A mixture of 400 mg (1.02 mmol) of compound 11, and 155 mg (1.02 mmol) of 4-(aminomethyl)benzoic acid dissolved in 10 mL of THF and 2 mL of $H_2O$ was treated with 1N NaOH in order to adjust the pH to 8.5–9. The reaction was stirred for 3 h at ambient temperature with the addition of base as needed to maintain the pH at 8.5–9. The THF was removed under vacuum, and 10 mL of $H_2O$ was added. The pH was lowered to 5.5–6 with 1N HCl, and the precipitate which formed was collected by centrifugation. The solid was washed with water and dried under vacuum to give a recoverable yield of 96 mg (22% yield) of compound 12 as a white solid.

EXAMPLE 13
Synthesis of the TCP Analog, (Compound 13)

A mixture of 82.2 mg (0.193 mmol) of compound 12, 110.9 mg (0.963 mmole) of N-hydroxysuccinimide and 92.3 mg (0.482 mmol) of 1-(3-dimethylaminopropyl)-3-ethylcarbodiimide hydrochloride was stirred in 5 mL of anhydrous DMF and 20 mL anhydrous $CH_2Cl_2$ (distilled from $CaH_2$) at ambient temperature under argon overnight. The reaction mixture was diluted to 40 mL with $CH_2Cl_2$, washed twice with 40 mL of sat. $NaHCO_3$, once with 40 mL of $H_2O$, and once with 40 mL of sat. NaCl, and then dried over $Na_2SO_4$. The solvent was removed under reduced pressure, and the resulting solid was purified by chromatography on flash grade silica eluted with 1:1:1 THF (distilled over sodium/benzophenone)/EtOAc/hexane to give 82 mg (81% yield) of compound 13 as a white solid.

EXAMPLE 14
Synthesis of the Succinylated TCP Analog (Compound 14) (Scheme IV)

To a solution of 200 mg (0.802 mmol) of Tenocyclidine (TCP) and 121 mg (1.203 mmol) of succinic anhydride in 10 mL of distilled $CH_2Cl_2$ cooled in an ice-water bath was added 428 mg (3.207 mmol) of aluminum(III) chloride and the reaction mixture was stirred overnight, with no further cooling. An additional 121 mg (1.203 mmol) of succinic anhydride and 107 mg (0.802 mmol) of aluminum(III) chloride were added and the reaction was stirred for an additional 2 days. The reaction was quenched with 1N HCl, the pH adjusted to ~6.5 to 7 with 6N NaOH, and the resulting mixture filtered through a sintered glass funnel to remove aluminum salts. The layers were separated, and the aqueous phase was extracted once with $CH_2Cl_2$ and twice with EtOAc. The aqueous phase was saturated with sodium chloride and again extracted with EtOAc. All of the organic extracts were combined and evaporated. More product was recovered by evaporation of the aqueous phase to dryness, trituration of the resulting solid with ethanol, filtration, and evaporation of the ethanolic extract to dryness. The solids obtained from all the organic extracts were combined (280 mg) and purified by chromatography on flash grade silica gel eluted with 15% $MeOH/CHCl_3$ to give 182 mg (65%) of the product.

EXAMPLE 15
Preparation of Drug-BSA Conjugate of Compound 5

Conjugation of the PCP derivative (Compound 5) to bovine serum albumin (BSA) was performed as follows: To a solution of BSA (approximately 57 mg/mL) in 50 mM potassium phosphate, pH 8, (5 mL) (cooled in an ice bath), dimethylsulfoxide (DMSO) was added dropwise (5 mL). After warming to 25° C., a 5 mg/mL solution of the above mentioned derivative in DMSO (1 ml) was added dropwise. The reaction mixture was stirred at room temperature for 16 hours and then transferred to dialysis tubing and dialyzed first against 15 volumes of 30% DMSO—potassium phosphate buffer (50 mM, pH 8), second against 20% DMSO - potassium phosphate buffer, and third against 10% DMSO—potassium phosphate buffer, and a forth for four times more against potassium phosphate buffer. [Overall Drug: BSA ratio =10:1]

EXAMPLE 16
Absorption of Antibodies to Microparticles

Carboxyl-modified blue polystyrene microparticles from Seradyn (0.3 micron particles) were first washed three times at 1% solids by centrifuiging in 20 mM, pH 6.1 MES (2-[N-morpholino]ethanesulfonic acid). The washed microparticles were then adjusted to 5% solids in MES and (i) sensitized with 2 mg/mL anti-PCP antibody for 16 hours at room temperature, (ii) blocked with BSA solution in MES for 1 hour at room temperature, then (iii) washed for three times at 1% solids in MES by centrifugation, and (iv) adjusted again to 5% solids. Before use, equal volumes of this latex and 35% w/v sucrose in MES were mixed.

EXAMPLE 17
Preparation of Membrane Strip

Mylar backed large pore size nitrocellulose (10–20 micron) from Millipore Corp. was cut into pieces of 15 cm in length and 5 cm in width. Solution of PCP-BSA conjugate (about 5 mg/mL) and anti-BSA monoclonal Ab (about 2 mg/mL), both in 50 mM potassium phosphate buffer pH 7.5, were dispensed using IVEK Corp. Digispense 2000™ system at the rate 1 µl/cm onto nitrocellulose at a distance respectively 2 cm and 1 cm from the 15 cm side. Nitrocellulose segments were allowed to dry for about 30 min. at 37° C. and then were blocked with 1% w/v polyvinyl alcohol (PVA, m.w. 13,000–23,000) solution in 20 mM TRIS, pH 8, for 30 min. at room temperature. The segments were then rinsed in water and dried.

Sample pads were prepared by cutting BioRad Laboratories gel blotter into 0.5 $cm^2$ pieces. The same BioRad gel blotter was used for the sink pads.

The same nitrocellulose as described above in this example was used as a separate membrane for microparticles (top membrane). For this purpose the nitrocellulose, which was previously blocked in the same manner as the main membrane, was cut into 5 mm wide strips and latex was applied using the IVEK dispensing system. After drying for 30 min. at 37° C., this membrane was placed, nitrocellulose surface down, onto the main membrane and laminated to the main membrane with Adhesive Research Inc. adhesive mylar. After this, the segment was cut into 5 mm wide strips, sample pad and sink pad were placed respectively at the beginning and terminal ends of the strips. The calibration curve was obtained by dipping the membrane strip in solutions containing predetermined amounts of the drug (PCP standards). The signal strength is determined as follows: 2.5=dark blue, 1.5=medium blue. 0.8=light blue, and 0=colorless. When the strip read colorless, a complete inhibition is achieved and the sample is indicated to contain 25 ng/mL of PCP.

FIG. 1 illustrates that free phencyclidine (PCP) competes with the drug conjugate compound 5 for binding with anti-PCP antibodies such that the presence of PCP results in a decrease or inhibition of the antibody-antigen binding and that this compound is useful as a reagent for the determination of PCP.

FIG. 2 illustrates that free phencyclidine (PCP) competes with the drug conjugate compound 12 for binding with anti-PCP antibodies such that the presence of PCP results in a decrease or inhibition of the antibody-antigen binding and that this compound is useful as a reagent for the determination of PCP.

Figure 3:
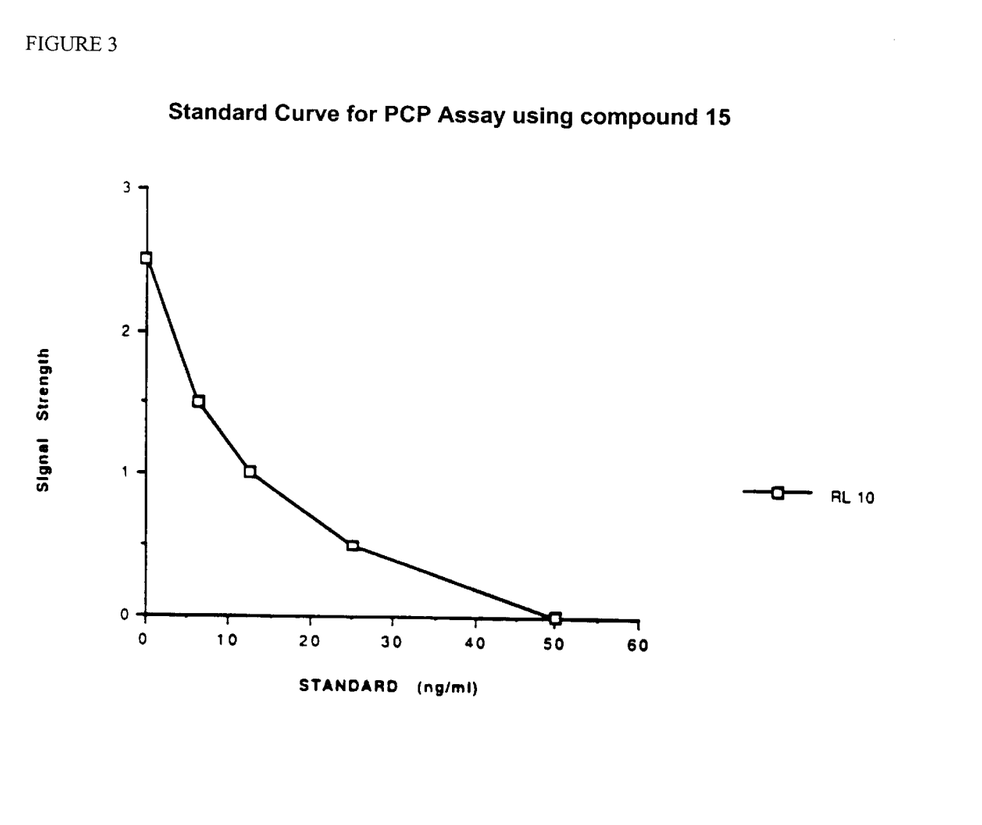
FIG. 3 illustrates competition between compound 15 and PCP.

FIG. 3 illustrates that free phencyclidine (PCP) competes with the drug conjugate compound 15 for binding with anti-PCP antibodies such that the presence of PCP results in a decrease or inhibition of the antibody-antigen binding and that this compound is useful as a reagent for the determination of PCP.

What is claimed is:

1. A compound of the formula:

wherein X is —OH or a reporter molecule selected from the group consisting of aminofluorescein and aminomethylfluorescein and n is an integer between 1 and 10, inclusive.

2. A compound of the formula:

3. A compound of the formula:

wherein wherein X is —OH or a reporter molecule selected from the group consisting of aminofluorescein and aminomethylfluorescein and n is an integer between 1 and 10, inclusive.

4. A compound of the formula:

5. A compound of the formula:

wherein X is —OH or a reporter molecule selected from the group consisting of aminofluorescein and aminomethylfluorescein and n is an integer between 1 and 10, inclusive.

6. A compound of the formula:

7. An immunoassay kit for detecting the presence of PCP in a sample comprising a solid support containing labeled anti-PCP antibody in a first region, and the compound of claim 2 immobilized in a second region.

8. An immunoassay kit for detecting the presence of PCP in a sample comprising a solid support containing labeled anti-PCP antibody in a first region, and the compound of claim 4 immobilized in a second region.

9. An immunoassay kit detecting the presence of PCP in a sample comprising a solid support containing labeled anti-PCP antibody in a first region, and the compound of claim 6 immobilized in a second region.

* * * * *

UNITED STATES PATENT AND TRADEMARK OFFICE
CERTIFICATE OF CORRECTION

PATENT NO. : 5,939,332  Page 1 of 1
DATED : August 17, 1999
INVENTOR(S) : Ghoshal et al.

It is certified that error appears in the above-identified patent and that said Letters Patent is hereby corrected as shown below:

<u>Title page,</u>
Item [75], Inventors, change "James C. Lee; Luis Fernando Del Corral, both of Memphis; Richard A. Clark, Collierville; Pedro A. Bonilla, Memphis, all of Tenn." to -- Mitali Ghoshal of Branchburg, Raymond A. Hui of Lyndhurst, James E. Towt of Gillette, and Robert S. Wu of West Orange, all of New Jersey. --

<u>Column 7,</u>
Lines 1-10, Scheme II, Compound 7:

change "  " to  --.

Signed and Sealed this

First Day of October, 2002

Attest:

JAMES E. ROGAN
Attesting Officer   Director of the United States Patent and Trademark Office